United States Patent [19]
Papanicolopoulos et al.

[11] Patent Number: 5,428,657
[45] Date of Patent: Jun. 27, 1995

[54] X-RAY MONITORING SYSTEM

[75] Inventors: Chris D. Papanicolopoulos, Stone Mountain; J. Craig Wyvill, Atlanta; Wayne D. R. Daley; William R. Owens, both of Stone Mountain, all of Ga.

[73] Assignee: Georgia Tech Research Corporation, Atlanta, Ga.

[21] Appl. No.: 216,037

[22] Filed: Mar. 22, 1994

[51] Int. Cl.⁶ .......................................... G01N 23/201
[52] U.S. Cl. .......................................... 378/86; 378/88; 378/90
[58] Field of Search .................... 378/86, 87, 88, 89, 378/90

[56] References Cited

U.S. PATENT DOCUMENTS

| | | | |
|---|---|---|---|
| 3,375,369 | 3/1968 | Goldman et al. | 250/51.5 |
| 3,710,104 | 1/1973 | Pavlik | 250/51.5 |
| 3,749,910 | 7/1973 | Carr-Brian et al. | 378/86 |
| 3,944,822 | 3/1976 | Dzubay | 250/272 |
| 4,081,676 | 3/1978 | Backman | 250/272 |
| 4,486,894 | 12/1984 | Page et al. | 378/46 |
| 4,799,247 | 1/1989 | Annis et al. | 378/86 X |
| 4,817,122 | 3/1989 | Badono et al. | 378/88 |
| 4,870,671 | 9/1989 | Hershyn | 378/124 |
| 4,916,719 | 4/1990 | Kawatra et al. | 378/46 |
| 4,959,848 | 9/1990 | Parobek | 378/46 |
| 4,974,247 | 11/1990 | Friddell | 378/90 |
| 5,020,084 | 5/1991 | Robertson | 378/46 |
| 5,029,337 | 7/1991 | MacKenzie et al. | 378/90 |
| 5,040,200 | 8/1991 | Ettinger et al. | 378/88 |
| 5,280,513 | 1/1994 | Meltzer | 378/86 X |

Primary Examiner—David P. Porta
Attorney, Agent, or Firm—Hopkins & Thomas

[57] ABSTRACT

The invention is a method and apparatus for identifying and pinpointing the location of unwanted pieces of material or defects in, for example, de-boned poultry pieces. The poultry pieces to be inspected are carried on a conveyor and passed under an impinging collimated X-ray beam. The Rayleigh scattering resulting is detected and measured, as is the Compton back scattering and the data is processed in a processing unit to determine the location and type of foreign matter involved. The ratio of the Rayleigh and Compton scattering is also determined and used to verify the identity of the foreign material. Transmitted X-rays, i.e., radioscopy, are used to normalize the data, and to aid in a pinpointing of the location of the unwanted material.

24 Claims, 4 Drawing Sheets

Optimum Rayleigh Scattering Angle For Fat($q_{max}$=.11), Muscle($q_{max}$=.16), and Bone($q_{max}$=.18) at Different Source Energies

| Energy (keV) | Optimum Scattering Angle q (in Degrees) | | |
|---|---|---|---|
| | FAT | MUSCLE/water | BONE |
| 20.0 | ~8.1 | ~11.2 | ~12.7 |
| 30.0 | ~5.4 | ~7.5 | ~8.5 |
| 40.0 | ~4.0 | ~5.6 | ~6.3 |
| 50.0 | ~3.2 | ~4.5 | ~5.1 |
| 55.6 | ~2.8 | ~4.1 | ~4.6 |
| 60.0 | ~2.7 | ~3.7 | ~4.2 |
| 70.0 | ~2.3 | ~3.2 | ~3.6 |
| 80.0 | ~2.0 | ~2.8 | ~3.2 |
| 90.0 | ~1.8 | ~2.5 | ~2.8 |
| 100.0 | ~1.6 | ~2.2 | ~2.5 |

*FIG. 3*

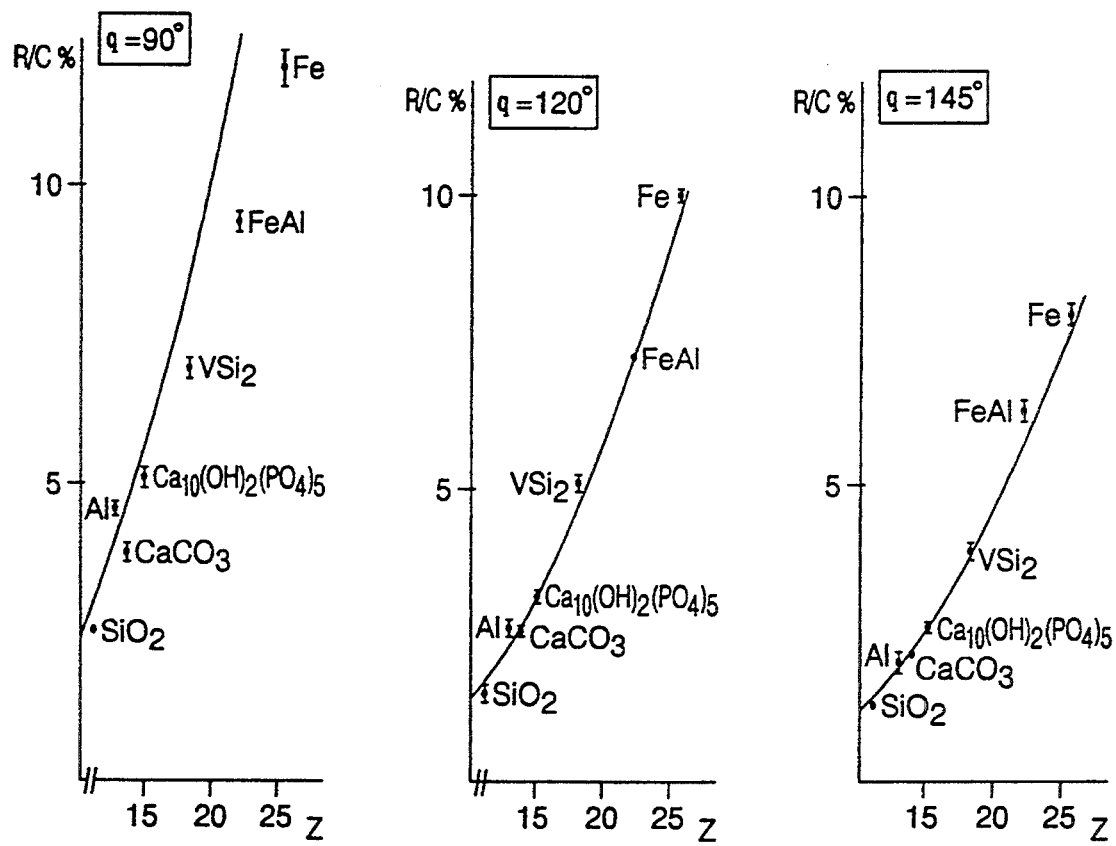

Measured R/C ratios for various compounds for incidence energy of E= 59.6 keV and different scattering angles: (a) scattering angle q = 90°, (b) scattering angle q = 120° and (c) scattering angle q = 145°.

*FIG. 4*

X-RAY MONITORING SYSTEM

FIELD OF INVENTION

This invention relates to X-ray screening of materials for the determination of the presence of additives or foreign matter therein and, more particularly, to a method and apparatus for determining the presence of, and for differentiating, unwanted materials or defects in a body from normally occurring matter or materials.

BACKGROUND OF THE INVENTION

While the principles and features of the present invention are applicable to the screening of a wide variety of materials, they are of particular utility in the screening of food products, e.g., meat, such as de-boned poultry pieces, and will be discussed and explained in that context.

Screening de-boned poultry pieces for the presence of bone and cartilage fragments or other defects is of vital concern to the poultry industry. Such fragments left in the meat can result in product liability actions and shipment returns for rework, with staggering cost implications. Manual "feeling" techniques are not accurate, pose a risk of spreading microbial contamination, are labor intensive, and are generally incapable of locating small fragments in the meat. As a consequence, systems have begun to be used in bone and cartilage screening which use typical X-ray transmission radioscopy techniques such as are used in airport security scanning. In such a system, differences in density between the meat and foreign matter are registered on the viewing screen. However, the density difference between the meat and bone or cartilage fragments is small, and material density variations in the meat created by water or fat, as well as meat thickness variations make it difficult for simple transmission X-ray techniques to discriminate accurately. As a consequence, with the X-ray transmission screening, false positive readings as high as fifty percent (50%) are not uncommon in poultry screening. Obviously, such lack of reliability can lead to increased expense in the processing of de-boned chicken parts, and can cause the rejection of parts that are, in actuality, perfectly acceptable.

In addition to transmission X-ray techniques, there are, in the prior art, systems which utilize "backscatter" detection of radiation from Compton scattering to enhance the image produced by the transmission radiation. A variation of such a system is shown in Friddell U.S. Pat. No. 4,974,247, wherein Compton radiation (backscatter) is detected along with reflected or backscattered transmission radiation from a reflector or illuminator to produce an enhanced radiographic image. While such an arrangement is not proposed specifically for poultry processing, it would appear that the basic principles thereof could be adapted to poultry screening.

In U.S. Pat. No. 3,944,822 of Dzubay there is shown an X-ray system for analyzing samples, such as, for example, a pellet of compressed orchard leaves, which relies upon photon fluorescence emitted by the sample when it is bombarded with X-rays. Different materials present in the sample have different characteristic florescence, hence, an analysis of the sample reveals the basic elements contained therein. The invention is directed to reducing the amount of Compton scattering relative to the florescent peaks, thereby enhancing the sensitivity of the fluorescent analysis. However, there are severe limitations to the detection of fluorescence, and hence, element composition, from small objects such as bone and cartilage pieces embedded within the bulk of a piece of chicken, for example. These limitations result from the fact that such materials, i.e., bone and cartilage fragments, have relatively low density, resulting in fluorescent intensities that are weak. In addition, there is substantial absorption of the fluorescence of, for example, calcium in bones and potassium in cartilage by the surrounding muscle and fat tissue of the sample. As a consequence, fluorescence analysis such as shown in the Dzubay patent is not practical for the rapid, continuous screening of chicken pieces in a processing production line. In such a production milieu, fluorescence is only useful for identifying foreign matter, such as oil or metal filings, on the surface of the sample, and thus is not practical for identifying bone and cartilage fragments.

various other prior art arrangements utilizing back scattering and/or fluorescence for sample screening are shown in Badono U.S. Pat. No. 4,817,122, et al., Page U.S. Pat. No. 4,486,894 et al., Pavlik U.S. Pat. No. 3,710,104, and Goldman U.S. Pat. No. 3,375,369 et al. None of these arrangements appears to lend itself to use in screening poultry products, for example, for the reasons set forth hereinbefore.

In the screening of poultry pieces, for example, it is desirable to locate and identify fragments of bone and cartilage with a high degree of accuracy and at a high rate of speed. Thus far, the prior art systems of screening samples fail in achieving one or more of these desiderata, with the consequence that the problems of product liability and shipment returns remain substantially the same as heretofore.

SUMMARY OF THE INVENTION

The present invention relies upon several X-ray interaction modes for achieving a precise and accurate analysis of the content and location of bone and cartilage fragments in pieces of poultry. The first mode is detection of Compton scattering which, as will be apparent hereinafter, for light element composition amorphous materials of similar density, such as skin, fat, or water pockets, is sensitive to density differences and inelastic scattering differences between the elements composing them. The second mode is detection of Rayleigh scattering which is sensitive to the presence of crystalline materials, such as bone, and which also improves contrast, i.e., clearly differentiates the crystalline material from the surrounding amorphous muscle and fat. The third mode is X-ray transmission, as is used in airport security systems, for example, and which is of aid in determining the precise location of the foreign matter fragments. In addition, the transmission mode is used to normalize the detected Compton and Rayleigh scatter fields which, without normalization, vary in intensity as a result in variations in sample thickness. In normalization, it is assumed that the transmitted X-rays travel through the same thickness of sample as the Compton and Rayleigh scattering, with similar effect. This thickness effect can then be eliminated from the Compton and Rayleigh readings by means of the transmission readings.

With these three X-ray modes, and the resultant detected intensities, the invention contemplates a fourth parameter, which is the ratio of Rayleigh-to-Compton (R/C) detected intensities. This ratio makes the differentiation of bone and cartilage from the muscle, fat, and water within the sample extremely accurate, inasmuch as the numerical value of the ratio for bone and cartilage is more than five times greater than for the muscle tissue. In addition, the R/C ratios for bone and cartilage can be determined and stored, for example, in a computer, for later comparison with instantaneous R/C ratios as determined by the computer from the measurements. This also has the added advantage of recognizing potentially false readings. Thus where, for example, the Rayleigh detector becomes so noisy that its readings may be misconstrued as being caused by a bone fragment, the R/C ratio will not be that of bone, hence the reading will be recognized by the computer as being false, i.e., not caused by a bone or cartilage fragment.

The apparatus of the invention, in a first illustrative embodiment thereof, comprises an X-ray source of sufficient energy and intensity to power the scatter fields which is positioned above a moving belt upon which are carried poultry samples to be scanned and screened. While it is preferable that the X-rays emitted by the source be as near monochromatic as possible, polychromatic X-rays are also acceptable despite the fact that there will be some contamination of the scatter. The beam of X-rays produced by the source is fan shaped so as to illuminate the width of the moving belt from edge to edge and has a thickness of approximately 1.5-2.0 mm. There will be some fall off in beam intensity from the center of the belt to the edges, but this and the known detector response can be compensated for by the computer, to which the various detected intensities are fed. Arrayed above the belt, on the same side thereof as the source, are Compton scattering detectors disposed at an angle to the beam direction. These detectors detect the intensity of the Compton scattering and their outputs are applied to the computer or processing unit.

Arrayed below the belt and at an angle to the direction of the beam are a plurality of Rayleigh scattering detectors which detect the intensity of the Rayleigh scattering which, as pointed out hereinbefore, is greatest for materials such as bone or cartilage. Also situated below the belt and aligned with the beam is an array of transmission type detectors which detect variations in the X-ray beam resulting from interception and alteration by particles imbedded within the poultry pieces. The outputs of the transmission, the Compton and Rayleigh scattering detectors are applied to the computer or processing unit. Preferably, the Compton, Rayleigh and transmission detectors have collimators to narrow the field of view to insure precise angle detection and eliminate false reading by the detectors from extraneous scatter.

The computer or processing unit, with the data thus supplied thereto, is able to pinpoint the location of extremely small aberrations, which may be due to skin folds, fat, water pockets, or bone or cartilage fragments, and to make a positive identification of whether it is bone or cartilage by determining the R/C ratio and comparing it to the known values of the ratio for bone or cartilage. The processing unit also normalizes the Rayleigh and Compton readings by means of the detected transmission beam.

While a fan type beam is used in the preferred embodiment, a thin pencil scanning beam may instead be used, with the appropriate mechanism for rapid side to side scanning over the width of the belt. Such a pencil beam can produce images of higher spatial resolution. It is also possible to locate an R/C detector in the form of a high energy resolution semiconductor detector at approximately 90° to the angle of incidence of the beam, for directly detecting the R/C ratio, thereby eliminating one computational step.

The preferred embodiment comprises a single measure or screening stage. It is also possible to divide the screening apparatus into two stages each having its own X-ray source and detecting only one of the scattering fields. Thus, one stage can detect Rayleigh scattering utilizing a low energy (−30 keV) X-ray source, and the other can detect Compton scattering utilizing a medium-high energy (−80 keV) X-ray source. It is also possible with such a two stage arrangement to place the Rayleigh detectors at the optimum location for the power source used to insure the best and most reliable results. With this arrangement, in real time, only energy changes in the X-ray beam and scattering are noted and it is not necessary to produce or develop a picture. As a consequence, very high speeds are possible.

The numerous features and advantages of the present invention will be more readily apparent from the following detailed description, read in conjunction with the accompanying drawings.

DESCRIPTION OF THE DRAWINGS

FIG. 3 is a table of optimum Rayleigh scattering angles for different materials and different X-ray energies;

FIG. 4 is a series of priorly known graphs of measured R/C ratios for various materials and different scattering angles.

DETAILED DESCRIPTION

In general, X-rays, a form of ionizing electromagnetic radiation, can penetrate matter and interact with the atoms of the different elements present. In some of these interactions, X-rays are absorbed and excite atoms (X-ray fluorescence) or bounce off atomic electrons, often changing direction and/or lose energy (scattering). Often some of the X-rays pass through the material without interactions and emerge substantially unchanged. All of these interactions always occur, and X-ray radiation specific to each interaction is always present.

Most industrial inspection systems are based upon X-ray imaging techniques, such as radiography and radioscopy, both of which are based upon X-ray absorption and its dependence upon the density of the materials traversed. Radiography records the transmitted X-ray intensities on special photographic film, which is then developed to produce negative or positive pictures. Radioscopy converts the transmitted X-ray intensities to a gray-line intensity image for display on a television screen, for example, for real time visual inspection. Of the two methods, radioscopy is better suited for continuous production line types of inspection, but it provides screen images of lesser spatial resolution. As a consequence, small defects or imbedded objects are often missed, and, in a manual mode, the radioscopy process depends upon the attention span and training of the observer. On the other hand, computer analysis of the radioscopy gray scale has proven more accurate. However, no level of data processing can alter the nature of the detected "observable", which is the difference in object and background intensity. Thus, in radioscopy, surface defects, such as folded skin or deep depressions, of a piece of poultry, and interstitial objects or defects, such as air, water, and fat pockets, of similar density or absorption to the surround bulk meat result in images which cannot be clearly differentiated by gray scale contrast, shape, or any other property present in the acquired data. In addition, the radioscopy system components and hardware are subject to aging, which introduces image "artifacts" into the imaging processing technique.

Figure 1:
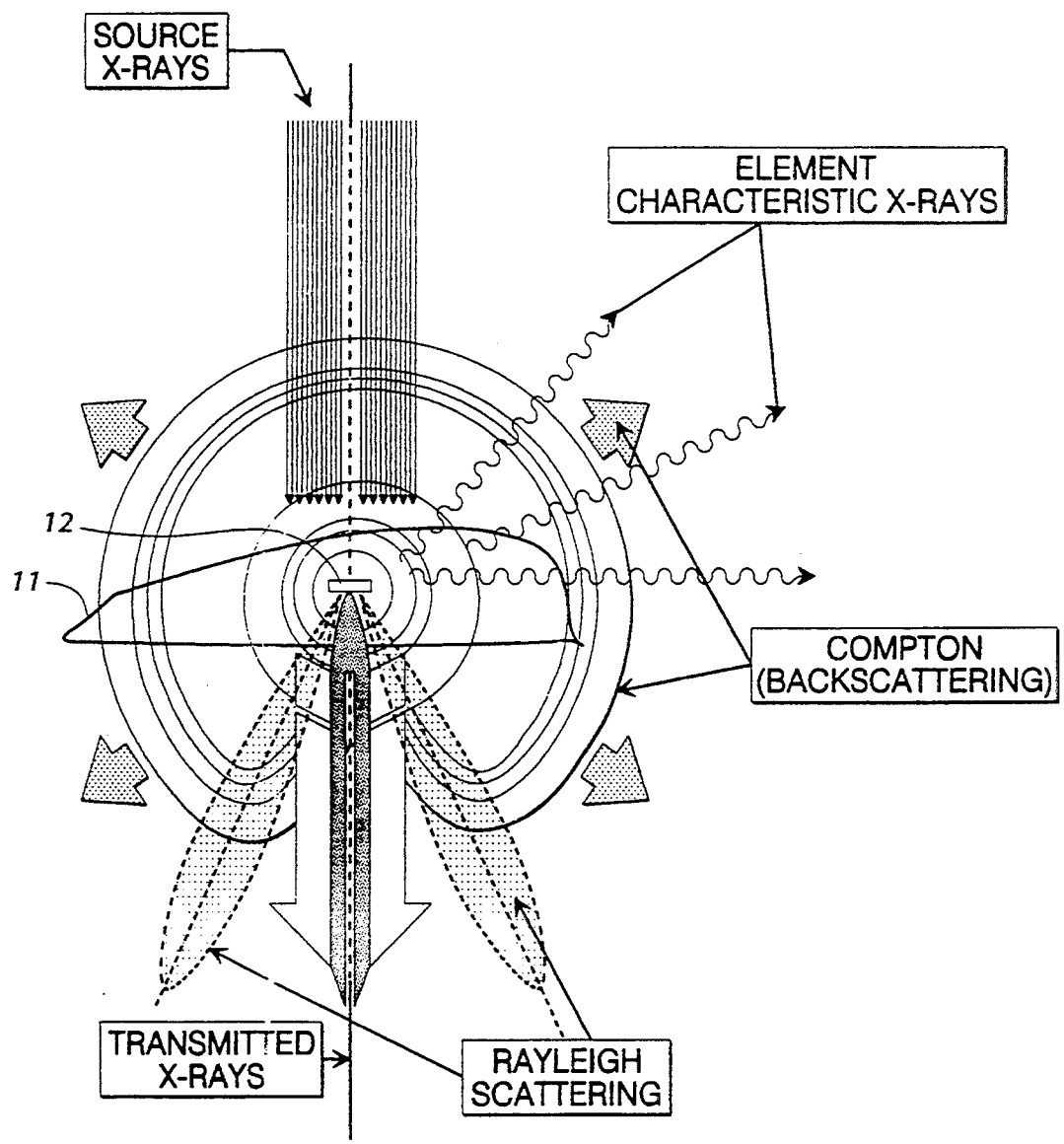
FIG. 1 is a diagram illustrating in concept the X-ray scattering phenomena of a foreign object in a piece of poultry.

The present invention is based upon the utilization of the other interactions, i.e., scattering of X-rays with the material being inspected which have, heretofore, in large part, been considered as unwanted interference in, for example, the radioscopy technique of inspection. In FIG. 1 some of these interactions are shown in concept for a piece of poultry 11 having embedded therein a foreign object 12. As can be seen in FIG. 1, the transmitted X-rays have an intensity variation resulting from the presence of, and partial absorption or blockage by, the object 12. In addition, structured matter (crystalline form) provides coherent scattering at specific angles and energies which are characteristic of the object (or material) structure and composition. This specific, coherent scattering, is known as Rayleigh scattering, and is less pronounced for amorphous materials such as muscle, water, fat, and the like. A second form of scattering, which is incoherent, is Compton scattering, which is caused, at least in part, by the presence of amorphous materials. Compton scattering is more pronounced for bone than for poultry meat and cartilage, hence, given a detectable difference in the Compton scattering between bone, cartilage, and meat, the detection of Compton scattering yields useful information in the inspection of de-boned poultry.

FIG. 1 also shows the element characteristic X-rays which are the product of induced X-ray fluorescence, and which are dependent on the composition of the foreign object within the material.

Figure 2:
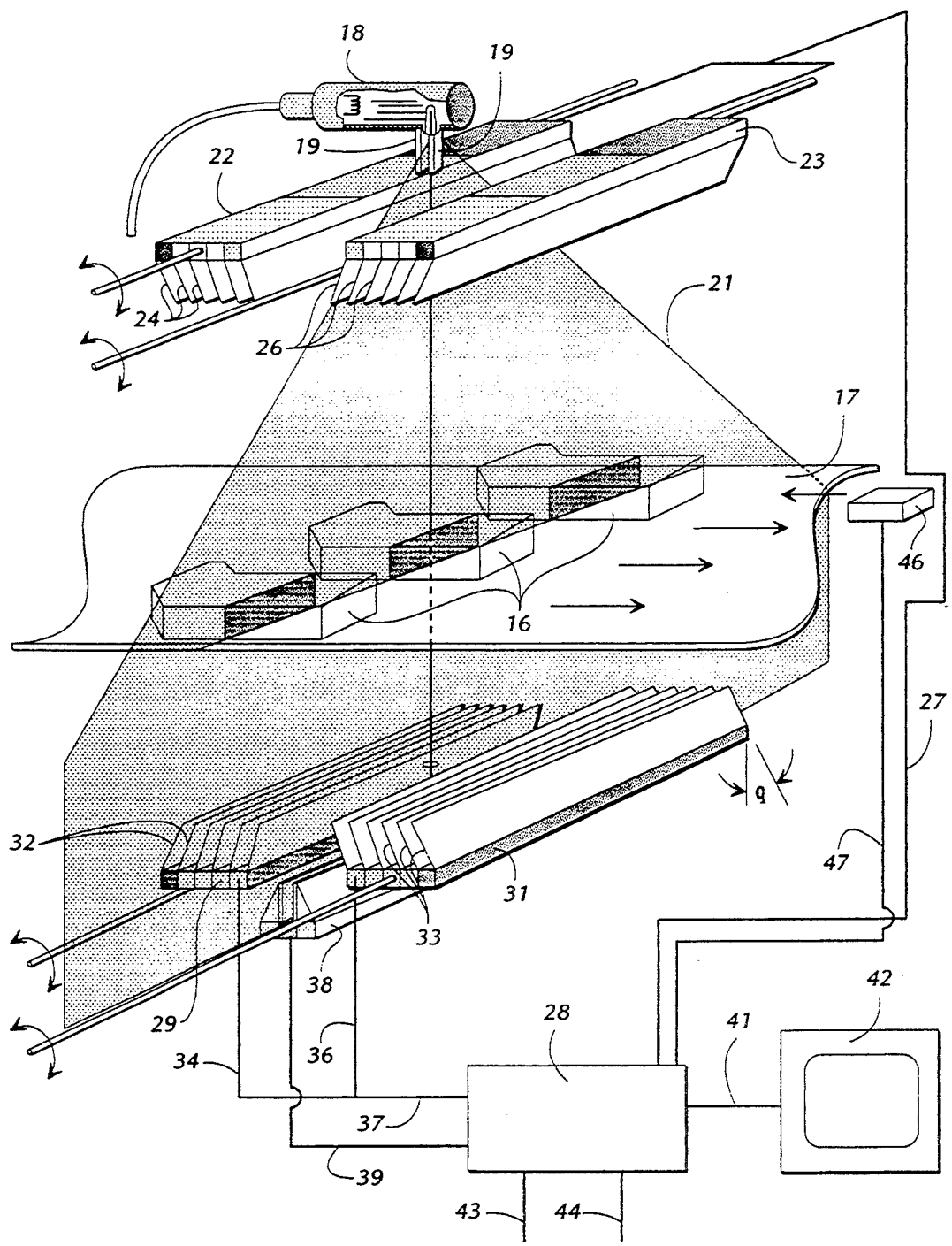
FIG. 2 is a perspective view of a preferred apparatus for practicing the method of the invention.

In FIG. 2 there is shown a preferred embodiment of the present invention as utilized in the inspection of a plurality of de-boned poultry pieces 16,16 traveling on a conveyor belt 17 in a poultry processing milieu. Located above the conveyor belt 17 is a source 18 of either monochromatic or polychromatic X-rays which, with suitable beam shaping means 19 produces a thin, (approximately 1.5–2.0 mm thick) fan-shaped collimated X-ray beam 21 which exceeds the width of the belt 17 at the plane thereof, so that all of the poultry pieces 16, 16 are impinged thereby.

Adjacent the source 18 on either side of the beam 21 is an array 22, 23 of Compton scattering detectors having collimators 24, 24 and 26, 26 respectively. The detector arrays 22, 23 and collimators 24, 24 and 26, 26 are preferably oriented at approximately a 90° angle to the plane of the conveyor 17 and hence the poultry pieces 16, 16. However, because of apparatus limitations, they are at less than a 90° angle, preferably in the range of 55° to 60° or more. The arrays can be rotated and height adjusted as indicated to achieve the best possible "aiming" for detecting the Compton back scattering. In addition, the collimators 24, 24 and 26, 26 narrow the viewing angle of the detectors themselves. The detectors may be any of a number of detector types, such as scintillator or intensity integration detectors, or semiconductor detectors such as silicon detectors, $HgI_2$, or CdTe detectors, which, although relatively expensive, operate at room temperature as opposed to some types of detectors requiring liquid nitrogen cooling. In practice it has been found that an array of detectors can be replaced by a single detector, or by a pair of detectors, which materially reduces the cost of the apparatus. The outputs of the detectors in arrays 22 and 23 is applied via lead 27 to a processing unit or computer 28 for signal processing, as will be discussed more fully hereinafter.

Positioned below conveyor 17, which is X-ray transparent or permeable, are first and second arrays 29, 31 of Rayleigh scattering detectors having collimators 32, 32 and 33, 33, respectively. The angle $\theta$ of the detectors relative to the beam 21 are important in determining which material is to be detected with the most efficiency. The detectors are arranged in rows, and each row is set at a different angle $\theta$ for detecting scattering from, for example, different materials. FIG. 3 is a table of optimum Rayleigh scattering angles, and hence detector angle, for fat, muscle/water, and bone at differing X-ray energy levels. It can be seen that for a beam energy level of 90 keV, optimum detection of bone requires that at least one row of detectors be placed at $\theta \approx 2.8°$. To this end, the arrays 29 and 31 may be rotated, or otherwise adjusted, as shown, to achieve the best detection angle $\theta$ for several different types of tissue simultaneously. In the table of FIG. 3, the parameter q is referred to as the "momentum transfer" coefficient. With the detector or detectors set at 2.8° and an energy of 90 keV, bone scattering will be the predominant radiation detected by the detectors in arrays 29 and 31. The collimators 32, 32 and 33, 33 must be capable of restricting the view of the scatter seen by the detectors to approximately 2.8°±0.1°, that is, to within one-tenth of a degree, to avoid inclusion of maximum muscle/water scatter occurring at 2.5° at this source energy. These figures are most accurate for monochromatic X-ray beams. On the other hand, for a polychromatic X-ray source, which includes most commercially available X-ray sources, a wide variety of different X-ray energies are emitted. Thus, if the detectors are angled at 2.8°, Rayleigh scattering from fat will be detected at 55.6 keV energy level, from muscle/water at 80 keV energy level, and from bone at 90 keV energy level. Thus, for a polychromatic beam, a precise choice of angle positioning and narrow collimation does not insure high resolution of the scatter from one particular tissue type. If the detectors have the additional property of discriminating detected X-rays by energy, such as a high energy resolution germanium semiconductor detectors, the detector can be made to respond only to, for example, the 90 keV scatter energy at a setting of 2.8°, thereby detecting the presence of bone.

The arrays 29 and 31 may comprise only a single detector, or a plurality of separate detectors "gated" to different spectral energy regions, may be used to detect Rayleigh scattering from other materials as well. It is also contemplated that in the case of several detectors, they may individually be oriented at a different angles $\theta$ for detection of a particular, different tissue by each detector. In such a case, fat, cartilage and bone may be detected and the fat reading subtracted from the others, then the cartilage readings, giving a more positive or enhanced bone reading. Which readings are to be subtracted depends upon what material it is desired to isolate or identify.

The outputs of the detectors in the arrays 29 and 31 are applied through leads 34,36 and 37 to the processing unit 28. Where, as noted in the foregoing, different detectors for each material are used, each detector output is to be applied separately to the unit 28.

The processing unit 28 examines both inputs from the Compton and Rayleigh detectors, as to signal strength, and utilizes them both to confirm each other. Thus, in the case of a particle of fat, the detected Compton scatter produces a "dark" region whereas the detected Rayleigh scatter produced by the "fat" detector array should produce a "bright" region. In the event that the Rayleigh detectors "misfire", the Compton detectors still confirm the existence of a particle of fat. Also, where a piece of bone, for example, is located near the surface of the poultry piece, the detected Compton scatter gives a more accurate indication than the detected Rayleigh scatter. On the other hand, for a deeply buried bone fragment, the detected Rayleigh scatter gives a more accurate indication. Thus the processing unit 28 uses both scatters to compliment each other. In addition, the detected Compton scatter enables the processing unit 28 to provide increased contract images to the monitor 42.

Also situated below conveyor 17 is a transmission X-ray detector array 38 comprising one or more detectors for detecting the X-rays transmitted through the poultry pieces 16. The detectors in array 38 make possible in conjunction with the scatter detection a determination of the precise location of foreign matter fragments in the pieces 16, while the Compton and Rayleigh scatter detection also identifies such foreign fragments as to physical composition. In addition, the transmission mode is used to normalize the detected Compton and Rayleigh scatter fields to alleviate scatter field intensity variations resulting in variations in the thickness of the poultry pieces 16. The output of detector array 38 is applied through lead 39 to the processing unit 28, which is programmed to effect such normalization.

As thus far described, the system depicted in FIG. 2 detects Compton scattering, Rayleigh scattering and X-ray transmission (radioscopy) and applies the detector outputs to a processing unit 28, one output of which is applied via a lead 41 to a viewing screen or monitor 42. The processor has further outputs 43 and 44 which may be used in any of a number of ways, such as for data printout, alarm systems, and the like. The processing unit 28 processes the received data to provide the desired identification of foreign material within the poultry pieces, to compensate for variations in incident X-ray beam intensities across the width of the fan shaped beam, and provides, if desired, visual and printed monitoring. There are, however, instances in which noise and the like can cause the detectors to render false readings which might be misconstrued as, for example, bone, where bone actually is not present. Thus, it is desirable to produce within the processor 28, or actually to measure and apply to the processor, a parameter which positively identifies bone, for example, and which, therefore, identifies false readings.

It is known that the ratio of Rayleigh scattering to Compton scattering (R/C) has a unique value for most materials, and it is especially useful in identifying and differentiating materials of low atomic number (Z). In FIG. 4 there are shown measured values in percent of the R/C ratio for different materials, at different scattering angles $\theta$, and for a single incident energy. It can be seen that, although the R/C value may differ slightly for different angles, the compound Hydroxyapatite $[Ca_{10}(OH)_2(PO_4)_6]$, which is the main mineral component of bone, is clearly identifiable by its RC value. Thus the R/C ratio gives a positive confirmation of the presence or absence of, for example, bone in the poultry pieces being scrutinized. The processor 28, preferably has stored in its memory pre-measured values of the R/C ratio at different incident energies and scattering angle $\theta$, and can thus, by constructing the instantaneous R/C ratio from ongoing scattering detection, positively identify bone or other foreign material detected and shown, for example on monitor 28. With the R/C ratios thus stored, aberrant readings from, for example, the Rayleigh scattering detectors, will be immediately identified as such inasmuch as the R/C ratio will not be the same as for the stored value for bone, for example. The processing unit 28 thus has available to it all of the information necessary to make determinations as to the presence of bone, cartilage, or other undesirable matter, and its precise location. By the utilization of the differing data inputs to confirm each other's indications, a substantially unambiguous determination is made which can be shown on the monitor 42, indicated on a printout, used to trigger an alarm, or, in a more sophisticated arrangement, used to actuate mechanisms for automatically removing the offending poultry piece.

It is also possible to measure the R/C ratio directly, by means of a detector or detector array 46, wherein the detectors may be of the high purity germanium (Ge) type, oriented at approximately 90° to the angle of incidence of the beam. The output of such an array 46 is applied to processor 28 by means of lead 47. The R/C ratio determinations or measurements as a function of scattering angle, with emphasis on the Compton profiles are of particular interest for cartilage tissue, and are demonstratably the most reliable means for detection of such tissue.

The method and apparatus of the invention has been disclosed in a preferred embodiment as depicted in FIG. 2, wherein all measurements take place substantially simultaneously in a single stage (or at a single station along the conveyor). It is also possible to make the measurements in a two stage system to optimize the two principal measurements, i.e., the Compton and Rayleigh measurements. Inasmuch as Compton measurements are optimum at medium-high ($\sim$80 keV) energies, and Rayleigh measurements at low ($\sim$30 keV) energies, the two stage system permits the use of two separate X-ray energy sources.

Figure 5:
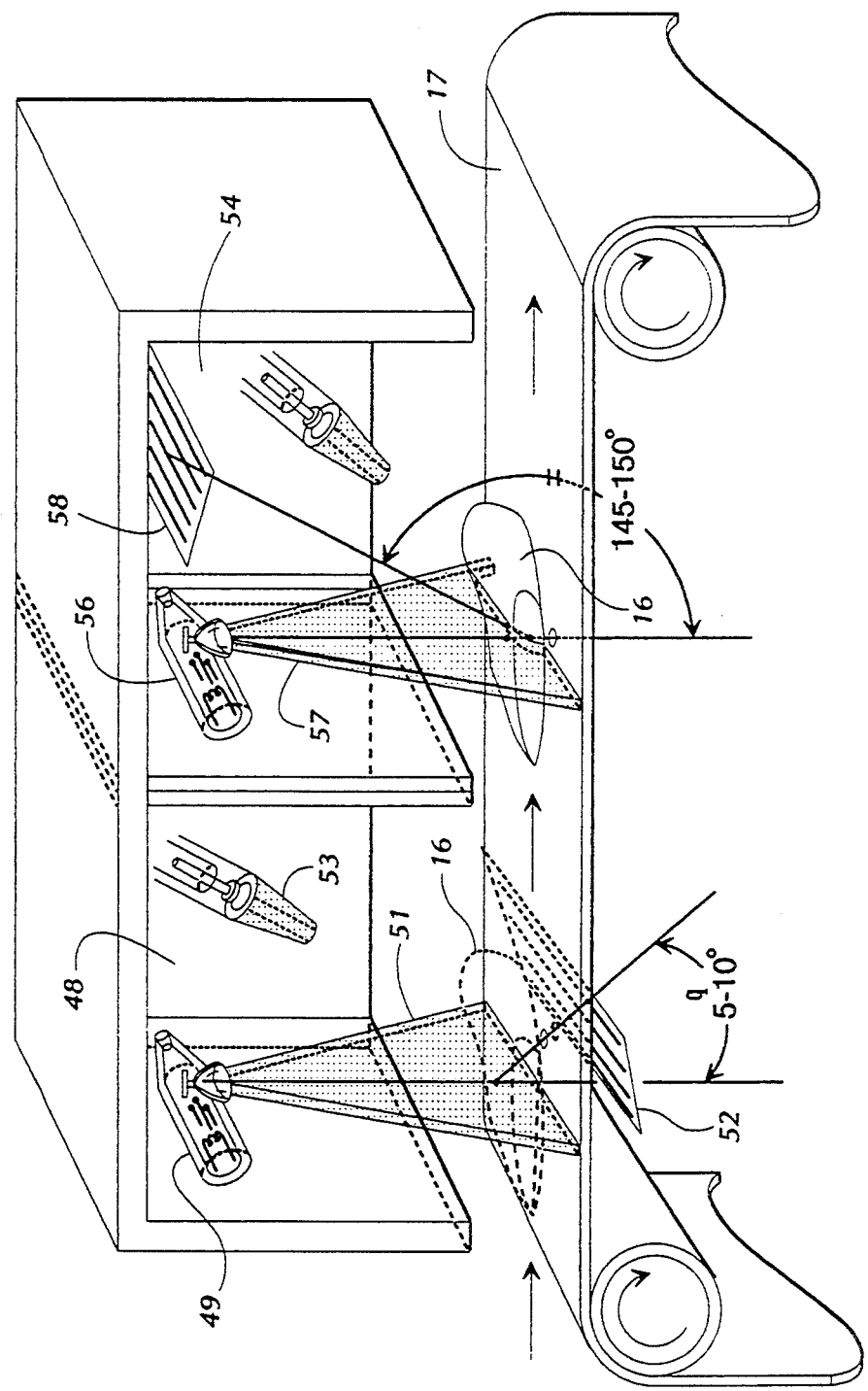
FIG. 5 is a perspective view of a portion of a second apparatus for practicing the method of the invention.

In FIG. 5 there is shown a portion of such a two-stage system, with connected processor hardware, including the display means, omitted for clarity. It is to be understood that such apparatus is also to be used with the system of FIG. 5.

The apparatus shown in FIG. 5 comprises a first station 48 having a first source 49 of low energy (30 keV) X-rays which directs a fan shaped beam 51 onto the poultry pieces 16, as shown. An imaging array 52 of Rayleigh scattering detectors, shown without collimators, is positioned below the conveyor at the desired angle $\theta$, as discussed hereinbefore for detecting the Rayleigh scattering from, for example, bone. Also located at station 48 is a detector 53 for detecting oil, metal particles, or other foreign matter on the surface of the poultry piece by means of X-ray fluorescence. A second station 54 has a second source 56 of X-rays of medium-to-high energy (~80 keV) which also directs a fan shaped beam 57 onto the poultry pieces 16, as shown. An imaging array 58 of Compton back scatter detectors is positioned above the conveyor 17 at an optimum angle for detecting Compton back scattering. Also located at station 54 is a detector 59 for detecting foreign matter on the surface of the poultry pieces 16 by means of X-ray fluorescence. It is also possible to include X-ray transmission detectors, not shown, in the apparatus of FIG. 5.

The arrangement of FIG. 5 permits Rayleigh scattering detection that is less contaminated with scatter from muscle, water and fat because of the absence of X-ray energies capable of generating such interference, due to the low-power X-ray source 49. Thus, the detectors used need not have the energy resolution necessary in the single stage apparatus of FIG. 2 and relatively inexpensive scintillation detectors can be used in place of the more expensive semiconductive detectors. In the two stage system, the results of imaging in one stage can provide spatial information as to the precise location over the width of the conveyor of bone or cartilage fragments, for example. This information is then forwarded (in the processing unit) to the next stage, and the processing unit can then "view" the data from detectors at the indicated locations for confirmation. Also, where the Rayleigh scattering detection unambiguously indicates bone fragments, for example, at a particular location in one or more of the poultry pieces, the Compton scattering detection can ignore, again within the processing unit, these particular locations, or whole pieces, for that matter, and concentrate only on the remaining pieces. It is also possible to have both Rayleigh and Compton scattering in both stages, thus, in effect, utilizing two of the assemblies of FIG. 2 in tandem, but with different X-ray energy sources in the two stages. This arrangement has the benefit of improving the Compton scattering images, and the added advantage of continuing operation despite a malfunction or breakdown is one of the stages.

In both of the arrangements of FIGS. 2 and 5, the acquisition of data is dependent, at least in part, upon the speed at which the conveyor 17 moves the pieces 16 past the fan shaped beam or beams. It has been found that a speed of approximately one foot per second, or a range of from one-half to one and one-half feet per second, is consistent with normal processing line rates while allowing adequate data collection. Other factors affecting data acquisition are the detector sensitivities and the X-ray source power. In every case, the apparatus can be fine tuned for the particular application.

From the foregoing, it can be seen that the method and system of the present invention constitute a reliable, substantially unambiguous way of determining the presence and precise location of unwanted substances in a piece or pieces of material, such as de-boned poultry pieces. As applied to poultry pieces, the system locates both bone and cartilage fragments and is capable of distinguishing them from muscle, fat, water and skin folds, for example. The principles and features of the invention are also applicable to materials other than poultry pieces with only minor modifications thereto.

The basic principles of the invention are susceptible to a wide range of applications. In examining a metal alloy of both heavy and light elements, for example, the Rayleigh scattering by the heavy elements can be compared to the Compton scattering of the light elements to determine the uniformity of distribution of these elements within the alloy. Printed circuit boards may be examined for integrity of circuitry and solder (lead) connections. The solder produces predominantly Rayleigh scattering and the circuitry produces predominantly Compton scattering. These detected scatterings may be compared within the processor with stored scattering standards for an ideal board to determine the quality of the circuitry and connections of the board under tests.

It is also possible, in the present system with minor variations, to measure one of the scatterings in advance of the others in, for example, a moving sample system. The remaining detectors can be maintained in a quiescent state until alerted or turned on, by the processing unit when the first or advance detector indicates an anomaly in the sample being tested, after which the remaining detectors perform their usual function in identifying the anomaly.

The foregoing has been by way of illustrating the principles and features of the method and apparatus of the present invention in illustrative embodiments thereof. Numerous variations or changes may occur to workers in the art without departure from the spirit and scope of the invention.

We claim:

1. A method of locating and identifying unwanted matter or defects in a piece of material comprising the steps of:
    directing a collimated X-ray beam onto the piece of material;
    detecting and measuring the Rayleigh scattering of X-ray energy from the material;
    detecting and measuring the Compton back-scatter of X-ray energy from the material;
    verifying the presence or absence of defects or unwanted matter and the location and identity thereof by comparing the scattering measurements;
    verifying the identity of the unwanted matter by determining the ratio of the Rayleigh-to-Compton measured scatter; and
    comparing the thus determined ratio to the known ratios for different materials to determine substantially unambiguously the identity of the unwanted matter.

2. The method as claimed in claim 1 and further comprising the step of detecting the X-ray energy transmitted through the material for locating the unwanted matter within the material.

3. The method as claimed in claim 2 and further comprising the step of normalizing the detected Compton and Rayleigh, scattering by means of the detected transmitted X-ray energy.

4. The method as claimed in claim 1 wherein the step of detecting and measuring the Rayleigh scattering comprises detecting such scattering at an angle $\theta$ to the angle of incidence of the X-ray beam wherein the angle $\theta$ varies from different types of unwanted matter and for different X-ray energies.

5. The method as claimed in claim 5 wherein the energy of the X-ray beam source is approximately 90 keV and the angle $\theta$ is approximately 2.8 degrees whereby bone is the unwanted matter detected.

6. The method as claimed in claim 4 wherein the energy of the X-ray beam source is approximately 30 keV and the angle $\theta$ is approximately 8.5 degrees whereby bone is the unwanted matter detected.

7. The method as claimed in claim 1 wherein the step of detecting and measuring the Compton back-scatter comprises detecting such scattering at an angle from 55° to 60° to the plane of the material being inspected.

8. A method of locating and identifying unwanted matter in poultry pieces comprising:
- forming and projecting an X-ray beam;
- conveying one or more poultry pieces through said beam;
- detecting first X-ray scattering from a poultry piece indicative of amorphous materials in the poultry piece;
- detecting second X-ray scattering from a poultry piece indicative of crystalline materials in the poultry piece;
- comparing the detection results to obtain a first approximation of the identity of the material causing the scattering;
- determining the value of the ratio of the second detected X-ray scattering to the first detected X-ray scattering; and
- determining whether the detected material is unwanted material by comparing the ratio value thus obtained t a set of known ratio values for various types of unwanted materials.

9. The method as claimed in claim 8 wherein the first X-ray scattering is Compton back-scattering.

10. The method as claimed in claim 8 wherein the second X-ray scattering is Rayleigh scattering.

11. The method as claimed in claim 10 and further including the step of varying the angle at which Rayleigh scattering is detected for optimizing the detection of scattering from a particular type of unwanted matter.

12. The method as claimed in claim 8 wherein the step of determining the value of the ratio comprises measuring the ratio directly.

13. The method as claimed in claim 8 and further including the step of directly detecting X-ray energy that passes straight through the poultry pieces without scatter.

14. An apparatus for inspecting one or more material pieces for the presence therein of pieces of unwanted matter comprising:
- a conveyor or member for transporting the material pieces;
- a source of X-rays mounted over said conveyor member for directing a collimated beam of X-rays toward said conveyor member and the material pieces thereon;
- first means situated below said conveyor for detecting a first type of X-ray scattering from said material pieces;
- second means situated above said conveyor means for detecting a second type of X-ray scattering from said material pieces; and
- third means for determining the ratio of said detected first type of scattering to said detected second type of scattering;
- whereby the matter causing said scattering is substantially unambiguously identified.

15. The apparatus as claimed in claim 14 and further comprising fourth means positioned below said conveyor of detecting X-ray transmission straight through the material pieces.

16. The apparatus as claimed in claim 14 wherein said first type of X-ray scattering is Rayleigh scattering.

17. The apparatus as claimed in claim 14 wherein said second type of scattering is Compton scattering.

18. The apparatus as claimed in claim 14 wherein said third means comprises a processing unit for receiving the detected scatter signals and forming the ratio.

19. The apparatus as claimed in claim 18 wherein said third means includes means for storing predetermined ratio values for different types of unwanted matter, and compares the determined ratio with the stored ratios to identify the matter causing the scattering.

20. The apparatus as claimed in claim 14 wherein said third means comprises detector means for directly measuring the ratio.

21. The apparatus as claimed in claim 14 and further including Rayleigh detector collimating means for collimation of the detected Rayleigh scattering.

22. The apparatus as claimed in claim 14 and further including Compton detector collimating means for collimation of the detected Compton scattering.

23. The apparatus as claimed in claim 14 and further including transmitted X-ray detector collimating means for collimation of the detected transmitted X-rays.

24. The apparatus as claimed in claim 23 and further including Rayleigh detector collimating means and Compton detector collimating means.

* * * * *